US009884872B2

(12) United States Patent
Li

(10) Patent No.: US 9,884,872 B2
(45) Date of Patent: Feb. 6, 2018

(54) ORGANIC COMPOUNDS

(71) Applicant: Intra-Cellular Therapies, Inc., New York, NY (US)

(72) Inventor: Peng Li, New Milford, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/320,280

(22) PCT Filed: Jun. 22, 2015

(86) PCT No.: PCT/US2015/036890
§ 371 (c)(1),
(2) Date: Dec. 19, 2016

(87) PCT Pub. No.: WO2015/196186
PCT Pub. Date: Dec. 23, 2015

(65) Prior Publication Data
US 2017/0197974 A1    Jul. 13, 2017

Related U.S. Application Data

(60) Provisional application No. 62/015,147, filed on Jun. 20, 2014.

(51) Int. Cl.
| C07D 487/14 | (2006.01) |
|---|---|
| C07B 59/00 | (2006.01) |
| A61K 45/06 | (2006.01) |
| A61K 31/519 | (2006.01) |
| A61K 9/00 | (2006.01) |
| A61K 8/49 | (2006.01) |
| A61Q 7/00 | (2006.01) |

(52) U.S. Cl.
CPC .......... *C07D 487/14* (2013.01); *A61K 8/4953* (2013.01); *A61K 9/0048* (2013.01); *A61K 31/519* (2013.01); *A61K 45/06* (2013.01); *A61Q 7/00* (2013.01); *C07B 59/002* (2013.01); *C07B 2200/05* (2013.01)

(58) Field of Classification Search
CPC .................................................. C07D 487/14
See application file for complete search history.

(56) References Cited

U.S. PATENT DOCUMENTS

| 5,202,328 A | 4/1993 | de Laszlo et al. |
|---|---|---|
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,221,335 B1 * | 4/2001 | Foster .................. C07B 59/002 424/1.81 |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,440,710 B1 * | 8/2002 | Keinan ................... C12P 13/02 435/147 |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,603,008 B1 * | 8/2003 | Ando ................... C07D 405/14 546/269.7 |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 7,517,990 B2 * | 4/2009 | Ito ......................... C07B 59/002 546/184 |
| 8,273,750 B2 | 9/2012 | Li et al. |
| 8,273,751 B2 | 9/2012 | Li et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2004/0087517 A1 | 5/2004 | Burnet et al. |
| 2004/0259792 A1 | 12/2004 | Palmer et al. |
| 2005/0075795 A1 | 4/2005 | Pandit |

(Continued)

FOREIGN PATENT DOCUMENTS

| DE | 199 31 206 A1 | 1/2001 |
|---|---|---|
| EP | 0 063 381 A1 | 10/1982 |
| EP | 0 095 289 A2 | 11/1983 |
| EP | 0 201 188 A2 | 12/1986 |

(Continued)

OTHER PUBLICATIONS

Dyck, Journal of Neurochemistry, vol. 46, Issue 2, pp. 399-404 (1986).*
Tonn, Biological Mass Spectrometry, vol. 22, Issue 11, pp. 633-642 (1993).*
Haskins, Biomedical Spectrometry, vol. 9 Issue 7, pp. 269-277 (1982).*
Wolen, J. of Clinical Pharmacology 1986; 26: pp. 419-424.*
Browne, J. of Clinical Pharmacology, 1998; 38: pp. 213-220.*
Baillie, Pharmacology Rev.1981; 33: pp. 81-132.*
Gouyette, Biomedical and Environmental Mass Spectrometry, vol. 15, pp. 243-247 (1988).*
Cherrah, Biomedical and Environmental Mass Spectrometry, vol. 14 Issue 11, pp. 653-657 (1987).*

(Continued)

*Primary Examiner* — Erich A Leeser
(74) *Attorney, Agent, or Firm* — Hoxie & Associates LLC

(57) ABSTRACT

Provided are PDE1 inhibitors of Formula I, processes for their production, their use as pharmaceuticals, and pharmaceutical compositions comprising them.

18 Claims, No Drawings

(56) References Cited

U.S. PATENT DOCUMENTS

| | | | |
|---|---|---|---|
| 2005/0113379 A1 | 5/2005 | Ge et al. | |
| 2006/0252790 A1 | 11/2006 | Allen et al. | |
| 2007/0082929 A1* | 4/2007 | Gant | C07D 401/12 |
| | | | 514/338 |
| 2007/0197695 A1* | 8/2007 | Potyen | C08K 5/55 |
| | | | 524/110 |
| 2008/0176961 A1 | 7/2008 | Greengard et al. | |
| 2008/0188492 A1 | 8/2008 | Li et al. | |
| 2008/0193964 A1 | 8/2008 | Greengard et al. | |
| 2008/0194592 A1 | 8/2008 | Mates et al. | |
| 2010/0087450 A1 | 4/2010 | Mates et al. | |
| 2010/0173878 A1 | 7/2010 | Li et al. | |
| 2010/0273753 A1 | 10/2010 | Li et al. | |
| 2010/0273754 A1 | 10/2010 | Li | |
| 2010/0323997 A1 | 12/2010 | Fienberg et al. | |
| 2011/0237561 A1 | 9/2011 | Li et al. | |
| 2011/0245214 A1 | 10/2011 | Li et al. | |
| 2011/0281832 A1 | 11/2011 | Li et al. | |
| 2011/0312978 A1 | 12/2011 | Davis et al. | |
| 2012/0053190 A1 | 3/2012 | Fienberg et al. | |
| 2012/0071450 A1 | 3/2012 | Li et al. | |
| 2012/0094966 A1 | 4/2012 | Li et al. | |
| 2012/0136013 A1 | 5/2012 | Li et al. | |
| 2012/0201754 A1 | 8/2012 | Li | |
| 2012/0238589 A1 | 9/2012 | Li et al. | |
| 2013/0018063 A1 | 1/2013 | Li et al. | |
| 2013/0085123 A1 | 4/2013 | Li et al. | |
| 2013/0239234 A1 | 9/2013 | Greengard et al. | |
| 2013/0324565 A1 | 12/2013 | Li et al. | |
| 2013/0331363 A1 | 12/2013 | Li et al. | |
| 2013/0338124 A1 | 12/2013 | Li et al. | |
| 2014/0005155 A1 | 1/2014 | Li et al. | |
| 2014/0011783 A1 | 1/2014 | Li et al. | |
| 2014/0148421 A1 | 5/2014 | Li et al. | |

FOREIGN PATENT DOCUMENTS

| | | |
|---|---|---|
| EP | 0 636 626 A1 | 2/1995 |
| EP | 0 911 333 A1 | 4/1999 |
| JP | 53031694 A | 3/1978 |
| KR | 10-1991-0006866 | 9/1991 |
| WO | WO 91/19719 A1 | 12/1991 |
| WO | WO 94/19351 A1 | 9/1994 |
| WO | WO 98/46606 A1 | 10/1998 |
| WO | WO 98/52568 A1 | 11/1998 |
| WO | WO 01/27113 A2 | 4/2001 |
| WO | WO 02/074312 A1 | 9/2002 |
| WO | WO 03/002567 A1 | 1/2003 |
| WO | WO 03/020702 A2 | 3/2003 |
| WO | WO 03/020724 A1 | 3/2003 |
| WO | WO 03/042216 A1 | 5/2003 |
| WO | WO 2006/133261 A2 | 12/2006 |
| WO | WO 2007/143568 A1 | 12/2007 |
| WO | WO 2007/143705 A2 | 12/2007 |
| WO | WO 2008/063505 A1 | 5/2008 |
| WO | WO 2009/073210 A1 | 6/2009 |
| WO | WO 2009/075784 A1 | 6/2009 |
| WO | WO 2010/065151 * | 6/2010 ........... C07D 491/00 |
| WO | WO 2010/065151 A1 | 6/2010 |
| WO | WO 2011/043816 A1 | 4/2011 |
| WO | WO 2011/153129 A1 | 12/2011 |
| WO | WO 2011/153135 A1 | 12/2011 |
| WO | WO 2011/153136 A1 | 12/2011 |
| WO | WO 2011/153138 A1 | 12/2011 |
| WO | WO 2012/171016 A1 | 12/2012 |
| WO | WO 2013/192556 A2 | 12/2013 |

OTHER PUBLICATIONS

Pieniaszek, J. Clin. Pharmacol.; 39: pp. 817-825 (1999).*
Honma et al., Drug Metab. Dispos. 15 (4): 551 (1987).*
International Search Report of International Application No. PCT/US2015/036890, prepared by the International Search Authority, dated Sep. 14, 2015, 4 pages.
U.S. Appl. No. 14/125,017, filed Mar. 17, 2014, Li et al.
U.S. Appl. No. 14/252,511, filed Apr. 14, 2014, Li et al.
Abstract for EP 0 063 381 A1 (WO8203626A1).
Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, 1997, 40 (14), 2196-2210.
Al-Afaleq, E. et al., "Heterocyclic o-Aminonitriles: Preparation of Pyrazolo[3,4-d]—pyrimidines with Modification of the Substituents at the 1-Position," Molecules, 2001, 6, 621-638.
"Anxiety," [retrieved on May 14, 2008]. Retrieved online via Internet, URL: http://www.nlm.nih.gov/medlineplus/anxiety.html, 5 pages.
Aswar, M. et al., "Anti-Cataleptic Activity of Various Extracts of *Ocimum sanctum*," International Journal of Pharmaceutical Research and Development, 2010, 2 (6), 7 pages.
"Autism," [retrieved on May 14, 2008]. Retrieved online via Internet, URL: http://www.nlm.nih.gov/medlineplus/autism.html, 6 pages.
Banker, Gilbert S. et al., Eds., Modern Pharmaceutics, Third Edition, Marcel Dekker Inc., New York, 1996.
Bastia, E. et al., "Effect of $A_1$ and $A_{2A}$ Adenosine Receptor Ligands in Mouse Acute Models of Pain," Neuroscience Letters, 2002, 328, 241-244.
Bender, A. et al., "Cyclic Nucleotide Phosphodiesterases: Molecular Regulation to Clinical Use," Pharmacological Reviews, 2006, 58 (3), 488-520.
Blokland, A. et al., "PDE Inhibition and Cognition Enhancement," 2012, 22 (4), 349-354 (abstract only).
Boyd, K. et al., "Dopamine Receptor Signaling and Current and Future Antipsychotic Drugs" in Current Antipsychotics, Handbook of Experimental Pharmacology, 212, Gross, G. et al., Eds., doi:10. 1007/978-3-642-25761-2_3, Springer-Verlag, Berlin, 2012, pp. 53-86.
Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, 2000, 43 (25), 4850-4867.
Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.
Chebib, M. et al., "1-Phenylpyrazolo[3,4-d]pyrimidines; Structure-Activity Relationships for C6 Substituents at $A_1$ and $A_{2A}$ Adenosine Receptors," Bioorganic & Medicinal Chemistry, 2000, 8, 2581-2590.
Chen, M. et al., "Effects of Bimatoprost 0.03% on Ocular Hemodynamics in Normal Tension Glaucoma," Journal of Ocular Pharmacology and Therapeutics, 2006, 22 (3), 188-193.
Chermat, R. et al., "Adaptation of the Tail Suspension Test to the Rat," Journal de Pharmacologie (Paris), 1986, 17 (3), 348-350.
Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.
Dewald, H. et al., "Synthesis and Potential Antipsychotic Activity of 1H-Imidazo[1,2-c]pyrazolo[3,4-e]pyrimidines," Journal of Medicinal Chemistry, 1988, 31, 454-461.
Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.
Ennaceur, A. et al., "A New One-Trial Test for Neurobiological Studies of Memory in Rats. 1:Behavioral Data," Behavioural Brain Research, 1998, 31, 47-59.
Fienberg, A. et al., "DARPP-32: Regulator of the Efficacy of Dopaminergic Neurotransmission," Science, 1998, 281, 838-842.
Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.

(56) References Cited

OTHER PUBLICATIONS

Gelbin, M. et al., "Ketene-S,N-acetals as Synthons for Heterocycles, New Synthesis of Pyrimidinones," Journal Für Praktische Chemie, 1987, 329 (5), 753-766.
Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.
Greengard, P. et al., "Beyond the Dopamine Receptor: The DARPP-32/Protein Phosphatase-1 Cascade," Neuron, 1999, 23, 435-447.
Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.
Hulley, P. et al., "Cyclic AMP Promotes the Survival of Dopaminergic Neurons in vitro and Protects Them from the Toxic Effects of MPP$^+$," Journal of Neural Transmission [Supplementa], 1995, 46, 217-228.
Japanese Patent Office, Patent Abstracts of Japan, Abstract for JP 53031694 A, Date of publication of application Mar. 25, 1978, 1 page.
Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, 2005, 70, 2824-2827.
Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Klaissle, P. et al., "Physical Activity and Environmental Enrichment Regulate the Generation of Neural Precursors in the Adult Mouse *Substantia nigra* in a Dopamine-dependent Manner," BMC Neuroscience, 2012, 13, 132, doi:10.1186/1471-2202-13-132, 15 pages.
Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Lundqvist, T. et al., "Exploitation of Structural and Regulatory Diversity in Glutamate Racemases," Nature, 2007, 447, 817-822.
Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Murray, F. et al., "Expression and Activity of cAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, 2007, 292, L294-L303.
Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]—pyrimidine Derivatives," Bulletin of the Chemical Society of Japan, 1989, 62 (9), 3043-3045.
Park, E, et al., "Traumatic Brain Injury: Can the Consequences Be Stopped?" CMAJ, 2008, 178 (9), 1163-1170.
Pardo, C. et al., "Synthesis of 1-(p-Nitrobenzyl)Azoles and 1-(p-Nitrobenzyl)Benzazoles," OPPI Briefs , 2000, 32 (4), 385-390.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brains," Acta Physiologica Scandinavica, Supplementum 367, 1971, 1-48.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.
Wolff, M. Ed., Burger's Medicinal Chemistry and Drug Discovery, Fifth Edition, vol. I: Principles and Practice, John Wiley & Sons, New York, 1995, 975-977.
Xia, Y. et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.

\* cited by examiner

ORGANIC COMPOUNDS

CROSS REFERENCE TO RELATED APPLICATIONS

This application is a United States Application under 35 U.S.C. § 371 claiming benefit of PCT Application No. PCT/US2015/036890, filed on Jun. 22, 2015, which claims priority to and the benefit of U.S. Provisional Application No. 62/015,147, filed on Jun. 20, 2014, the contents of each of which are hereby incorporated by reference in their entireties.

TECHNICAL FIELD

The present invention relates to PDE1 inhibitory compounds of Formula I as described below, processes for their production, their use as pharmaceuticals and pharmaceutical compositions comprising them. These compounds are useful, e.g., in the treatment of diseases involving disorders of the dopamine D1 receptor intracellular pathway, such as, among others, schizophrenia, Parkinson's disease, depression, narcolepsy, psychosis, damage to cognitive function, cardiovascular disorders or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in human central nervous system tissue. PDE1A is expressed in the brain with high levels in the CA1 to CA3 layers of the hippocampus and cerebellum and at a low level in the striatum. PDE1B is predominately expressed in the striatum, dentate gyrus, olfactory tract and in the prefrontal cortex co-localized with the dopamine D1 receptor. Its expression generally correlates with brain regions having high levels of dopaminergic innervation. Although PDE1B is primarily expressed in the central nervous system, it is also present in neutrophils and has been shown to be involved in inflammatory responses in this cell type. PDE1C is more ubiquitously expressed in the brain and is expressed in the heart and vascular smooth muscle. It is a major phosphodiesterase in the human cardiac myocyte.

Cyclic nucleotide phosphodiesterases decrease intracellular cAMP and cGMP signaling by hydrolyzing these cyclic nucleotides to their respective 5'-monophosphates (5'AMP and 5'GMP), both of which are inactive with respect to the intracellular signaling pathways of the cyclic nucleotides. CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of adenylate cyclases, resulting in increased cAMP. This cyclic nucleotide in turn activates protein kinase A (PKA; cAMP-dependent protein kinase). Production of cGMP is known to occur in tissues involved in cognitive function through various stimulations such as nitric oxide production induced by high intracellular calcium levels and to subsequently activate protein kinase G (PKG; cGMP-dependent protein kinase). PKG and PKA phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphatase-1 (PP-1), thereby increasing the state of phosphorylation of substrate proteins such as the progesterone receptor (PR) which leads to induction of physiologic responses. D1 receptor signaling is disrupted in schizophrenia, contributing to cognitive impairment in the disease. The role of cAMP and cGMP in cognitive function has been well established in animal studies. Studies in rodents also have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin, and progesterone signaling pathways. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity that is a consequence of D2 receptor-mediated increases in intra-cellular calcium. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as schizophrenia, Parkinson's disease, restless leg syndrome, depression, narcolepsy and cognitive impairment such as cognitive impairment associated with schizophrenia. PDE1 inhibitors are also useful in diseases that may be alleviated by the enhancement of progesterone-signaling such as female sexual dysfunction.

There is thus a need for compounds that selectively inhibit PDE1 activity.

SUMMARY OF THE INVENTION

Previous publication WO 2009/075784 disclosed, among others, (6aR,9aS)-2-(4-(6-fluoropyridin-2-yl)benzyl)-5- methyl-3-(phenylamino)-5,6a,7,8,9,9a-hexahydrocyclopenta[4,5]imidazo[1,2-a]pyrazolo[4,3-e]pyrimidin-4(2H)-one as an inhibitor of PDE1. This compound undergoes significant metabolism at several positions including the aniline ring and the cyclopentane ring. The current invention provides for Compounds of Formula I wherein such metabolism is attenuated by the substitution of hydrogen atoms for deuterium atoms at key locations discovered by the inventors.

The invention provides a compound of Formula I:

Formula I

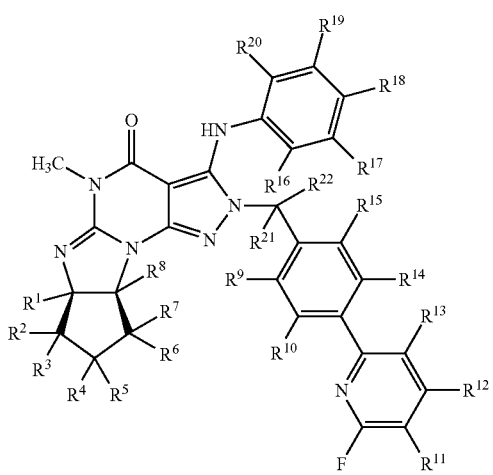

wherein $R_1$ through $R_{22}$ are each independently H or D (deuterium, $^2$H), provided that $R_1$ through $R_{22}$ are not all H,
in free or salt form.

In further embodiments, the invention provides compounds of Formula I as described in the following formulae:

1.1 The compound of Formula I, wherein one or more of $R^1$ through $R^{22}$ are D;
1.2 The compound of Formula I or 1.1, wherein $R^1$ is D, and any one or more of $R^2$ through $R^{22}$ are D;
1.3 The compound of Formula I or any of 1.1-1.2, wherein $R^8$ is D, and any one or more of $R^1$ through $R^7$ and $R^9$ through $R^{22}$ are D;
1.4 The compound of Formula I or any of 1.1-1.3, wherein $R^4$ and $R^5$ are D, and any one or more of $R^1$ through $R^3$ and $R^6$ through $R^{22}$ are D;
1.5 The compound of Formula I or any of 1.1-1.4, wherein $R^{18}$ is D, and any one or more of $R^1$ through $R^{17}$ and $R^{19}$ through $R^{22}$ are D;
1.6 The compound of Formula I or any of 1.1-1.5, wherein $R^1$ is D;
1.7 The compound of Formula I or any of 1.1-1.5, wherein $R^8$ is D;
1.8 The compound of Formula I or any of 1.1-1.5, wherein $R^{18}$ is D;
1.9 The compound of Formula I or any of 1.1-1.5, wherein $R^1$ and $R^8$ are D;
1.10 The compound of Formula I or any of 1.1-1.5, wherein $R^1$ and $R^{18}$ are D;
1.11 The compound of Formula I or any of 1.1-1.5, wherein $R^1$, $R^8$ and $R^{18}$ are D;
1.12 The compound of Formula I or any of 1.1-1.5, wherein $R^{16}$ through $R^{20}$ are all D;
1.13 The compound of Formula I or 1.1-1.12, wherein the compound is in substantially pure diastereomeric form (i.e., substantially free of other diastereomers);
1.14 The compound of any of Formula 1.1-1.12, wherein the remaining substituents of $R^1$ to $R^{22}$ that are not defined as D, are all H;
1.15 The compound of Formula I or 1.1-1.12, wherein the compound has a diastereomeric excess of greater than 70%, preferably greater than 80%, more preferably greater than 90%, and most preferably greater than 95%;

Compounds of the Invention, e.g., compounds of Formula I or any of Formulas 1.1-1.15, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. In one embodiment, the Compound of Formula I is in the form of the toluenesulfonic acid salt.

The invention also provides methods of making the Compounds of the Invention and methods of using the Compounds of the Invention for treatment of diseases and disorders as set forth below (especially treatment of diseases characterized by reduced dopamine D1 receptor signaling activity), such as schizophrenia, Parkinson's disease, Tourette's Syndrome, autism, fragile X syndrome, ADHD, restless leg syndrome, depression, cognitive impairment, e.g., cognitive impairment of schizophrenia, narcolepsy, central and peripheral neurodegenerative diseases, central and peripheral nervous system injuries and disorders (e.g. spinal cord injury, spinal muscular atrophy, motor neuron injury, axonal filament degradation, and motor neuron diseases, such as multiple sclerosis), cardiovascular diseases (including congestive heart failure, myocardial infarction, hypertension, atherosclerosis), cardiovascular dysfunction resulting from a muscular dystrophy (e.g., Duchenne muscular dystrophy) and diseases that may be alleviated by the enhancement of progesterone-signaling such as female sexual dysfunction or a disease or disorder such as psychosis or glaucoma). This list is not intended to be exhaustive and may include other diseases and disorders as set forth below.

In another embodiment, the invention further provides a pharmaceutical composition comprising a Compound of the Invention, in free, pharmaceutically acceptable salt, or in admixture with a pharmaceutically acceptable diluent or carrier.

DETAILED DESCRIPTION OF THE INVENTION

Methods of Making Compounds of the Invention

The Compounds of the Invention and their pharmaceutically acceptable salts may be made using the methods as described and exemplified herein and by methods similar thereto and by methods known in the chemical art. Such methods include, but are not limited to, those described below. If not commercially available, starting materials for these processes may be made by procedures, which are selected from the chemical art using techniques which are similar or analogous to the synthesis of known compounds.

Various starting materials, intermediates and/or Compounds of the Invention may be prepared using methods described or similarly described in WO 2006/133261, WO 2009/075784, and/or WO 2013/192556. All references cited herein are hereby incorporated by reference in their entirety.

The Compounds of the Invention may exist as diastereomers, racemates, polymorphs, hydrates, and/or solvates. Some compounds within the scope of this invention may contain one or more asymmetric centers. This invention includes the use of any of the optically pure stereoisomers as well as any combination of stereoisomers.

The synthetic methods disclosed in WO 2009/075784 and WO 2013/192556 are particularly applicable, as they include the methods to prepare the compound of Formula I-B. Those skilled in the art will readily see how those methods are applicable to the synthesis of the compounds of the present invention.

Formula I-B

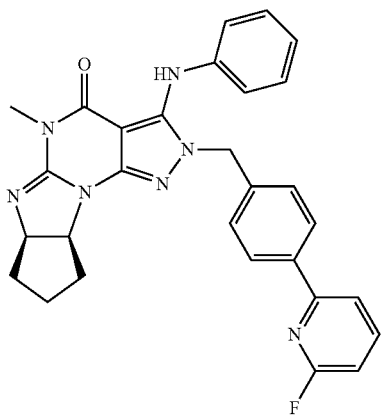

For example, Compounds of the Invention wherein any one or more of $R^1$ through $R^8$ are D, can be prepared from the corresponding aminocyclopentanol, according to the method described in WO 2009/075784 or WO 2013/192556. For example, by reacting said aminocyclopentanol, optionally as its acid salt, with Intermediate A in the presence of a coupling agent, e.g., benzotriazol-1-yloxy)tris(dimethylamino)phosphonium hexafluorophosphate (BOP reagent), and a base, e.g., 1,8-diazabicyclo[5.4.0]undec-7-ene (DBU), in a solvent such as tetrahydrofuran (THF). The intermediate alcohol is then cyclized by treatment with toluenesulfonyl chloride (TsCl) in the presence of one or more bases, such as dimethylaminopyridine (DMAP) and triethylamine (TEA) in a solvent, such as THF. The reaction is summarized in the following scheme:

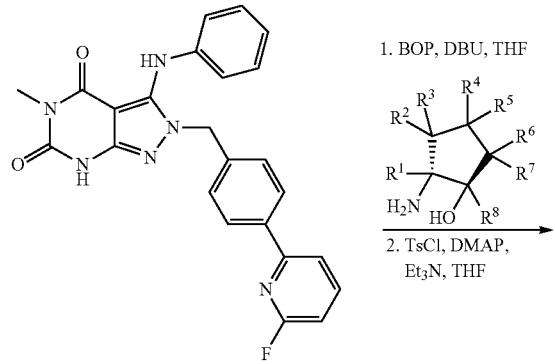

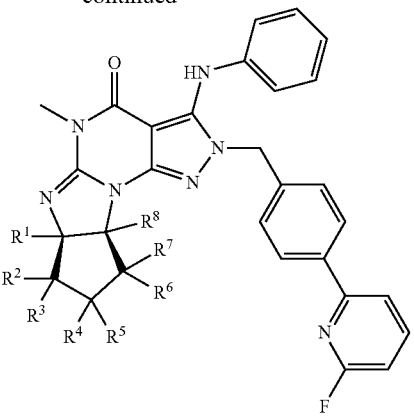

The required aminocyclopentanols can be prepared by methods known to those skilled in the art. For example, the aminocyclopentanol wherein $R^1$ is D can be prepared via a reductive amination procedure that uses a reducing agent such as sodium triacetoxyborodeuteride or sodium borodeuteride as the reducing agent. For example, an optionally protected (R)-2-hydroxycyclopentanone can be reacted with 4-methoxybenzylamine in the presence of sodium triacetoxyborodeuteride to yield the desired deuterated secondary amine, wherein P is the protecting group. Reaction of the resulting amine with a strong acid such as trifluoromethanesulfonic acid (TMFSA) will result in removal of the 4-methoxybenzyl group and the protecting group to yield the desired aminocyclopentanol. Those skilled in the art will know how to choose a suitable protecting group for the secondary alcohol such that deprotection can take place during the acid treatment step (e.g., a tert-butyldimethylsilyl group or a tert-butoxycarbonyl group). Alternatively, those skilled in the art could choose a protecting group that would survive this step. If desired, the protected intermediate can be purified by chiral HPLC in order to enhance the optical purity of the final product. The reaction is summarized in the scheme below:

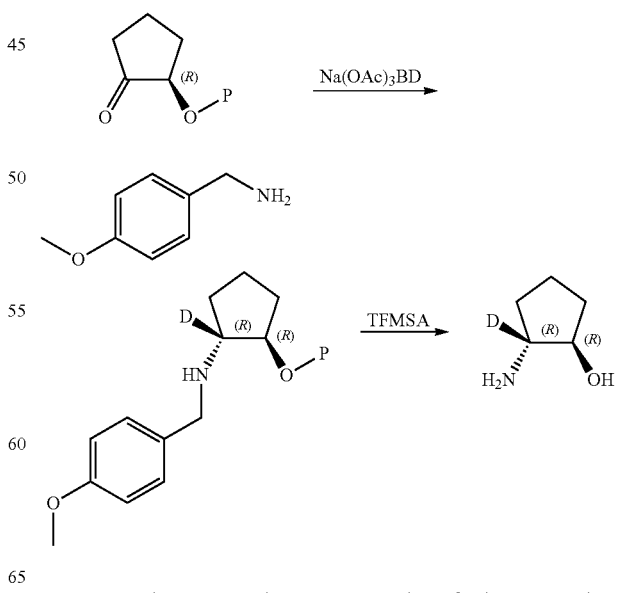

As another example, Compounds of the Invention wherein any one or more of $R^9$ to $R^{15}$ or $R^{21}$ to $R^{22}$ are D can be prepared from the corresponding benzyl halide, according to the method described in WO 2009/075784 or WO 2013/192556. For example, by reacting said benzyl halide with the Intermediate B in the presence of suitable base, such as cesium carbonate or potassium carbonate, in a suitable solvent, such as dimethylformamide or dimethylacetamide. The corresponding benzyl halide can be prepared by methods well known to those skilled in the art. The reaction is summarized in the following scheme:

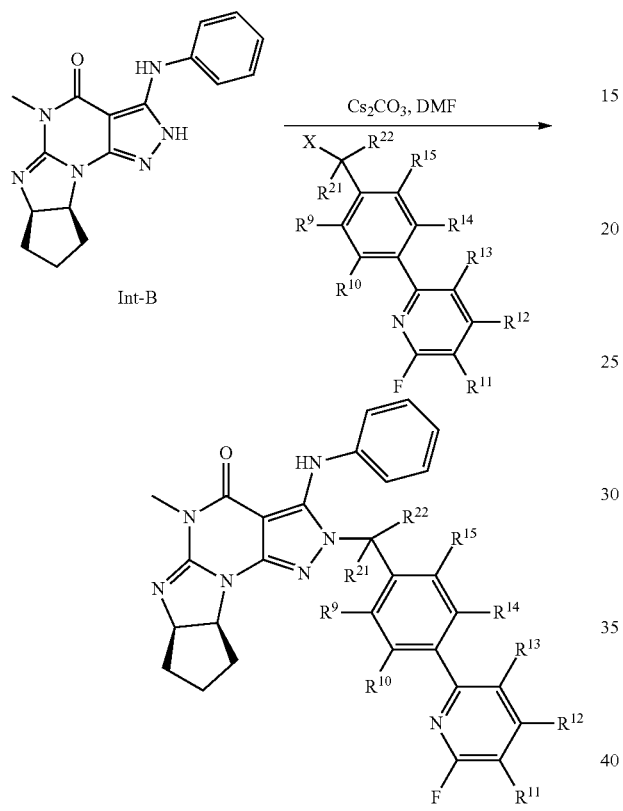

As another example, compounds of the invention wherein any one or more of $R^{16}$ to $R^{20}$ are D can be prepared from the corresponding phenyl isothiocyanate, according to the method described in WO 2009/075784 or WO 2013/192556. For example, by reacting said phenyl isothiocyanate with Intermediate C in a suitable solvent, such as dimethylformamide. The corresponding phenyl isothiocyanate can be prepared by methods well known to those skilled in the art. The reaction is summarized in the following scheme:

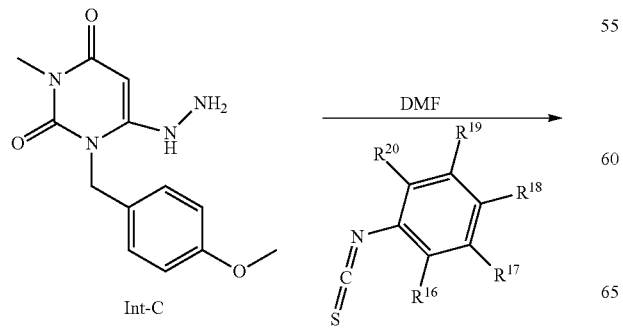

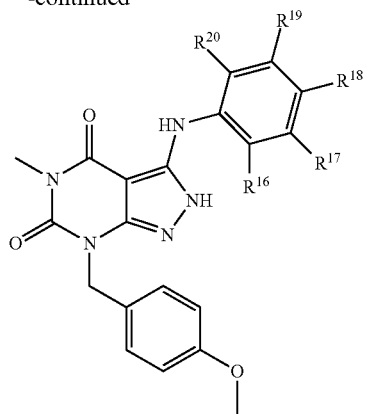

Alternatively, compounds of the invention wherein any one or more of $R^{16}$ to $R^{20}$ are D can be prepared from the corresponding aniline, according to the method described in WO 2009/075784 or WO 2013/192556. For example, by reacting said aniline with Intermediate D and a strong base, such as lithium hexamethyldisilylazide (LiHMDS), in a suitable solvent, such as THF at elevated temperature. Such a reaction can also be achieved by catalytic amination using a catalyst, such as tris(dibenzylideneacetone)dipalladium ($Pd_2(dba)_3$), and a ligand, such as Xantphos. The corresponding aniline can be prepared by methods well known to those skilled in the art. The reaction is summarized in the following scheme:

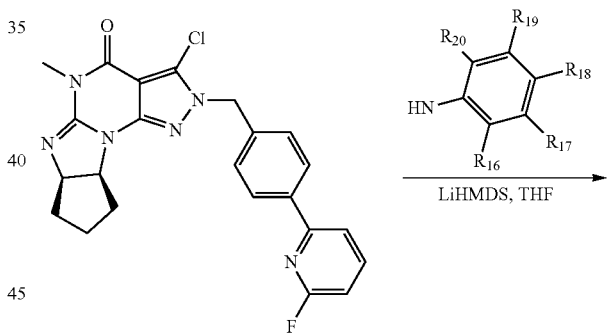

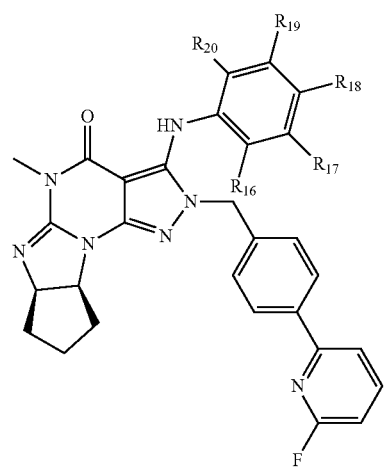

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg, tremors, dyskinesias, Huntington's disease, Alzheimer's disease, and drug-induced movement disorders;

(ii) Mental disorders, including schizophrenia, depression, attention deficit disorder, attention deficit hyperactivity disorder, bipolar illness, anxiety, sleep disorders, e.g., narcolepsy, cognitive impairment, e.g., cognitive impairment of schizophrenia, dementia, Tourette's syndrome, autism, fragile X syndrome, psychostimulant withdrawal, and drug addiction;

(iii) Circulatory and cardiovascular disorders, including cerebrovascular disease, stroke, congestive heart failure, atherosclerosis, myocardial infarction, cardiomyopathy, hypertension, essential hypertension, pulmonary hypertension (e.g., pulmonary arterial hypertension, pulmonary venous hypertension), cardiovascular dysfunction resulting from a muscular dystrophy (e.g., Duchenne Becker, limb-girdle, myotonic or Emery-Dreifuss muscular dystrophies), and sexual dysfunction, and cardiovascular diseases and related disorders as described in International Application No. PCT/US2014/16741, the contents of which are incorporated herein by reference;

(iv) Respiratory and inflammatory disorders, including asthma, chronic obstructive pulmonary disease, and allergic rhinitis, as well as autoimmune and inflammatory diseases;

(v) Diseases that may be alleviated by the enhancement of progesterone-signaling, such as female sexual dysfunction;

(vi) A disease or disorder such as psychosis, glaucoma, or elevated intraocular pressure;

(vii) Traumatic brain injury;

(viii) Any disease or condition characterized by low levels of cAMP and/or cGMP (or inhibition of cAMP and/or cGMP signaling pathways) in cells expressing PDE1; and/or (ix) Any disease or condition characterized by reduced dopamine D1 receptor signaling activity, (x) Central nervous system (CNS) and peripheral nervous system (PNS) injuries and disorders characterized, e.g., by damage or loss of axons, neurons, or glial cells, such as spinal cord injury, spinal muscular atrophy, cranial nerve injury, motor neuron injury, brain trauma, cerebral aneurysm related injury, axonal filament degradation, injury caused by epilepsy, injury caused by inflammation, injury caused by toxins, injury caused by radiation or chemotherapy, multiple sclerosis, peripheral neuropathies, sciatica, carpal tunnel syndrome, diabetic neuropathy, post-herpetic neuralgia, neuropathic pain syndrome, thoracic outlet syndrome, or other disorders or injuries that can be treated or prevented by axonal or neural growth or regeneration, as described in International Application No. PCT/US2014/30412, the contents of which are incorporated herein by reference;

comprising administering an effective amount of a Compound of the Invention, e.g., a compound according to any of Formulae I or 1.1-1.15, in free or pharmaceutically acceptable salt form, to a human or animal patient in need thereof.

In an especially preferred embodiment, the invention provides methods of treatment or prophylaxis for narcolepsy. In this embodiment, PDE1 Inhibitors may be used as a sole therapeutic agent, but may also be used in combination or for co-administration with other active agents. Thus, the invention further comprises a method of treating narcolepsy comprising administering simultaneously, sequentially, or contemporaneously therapeutically effective amounts of (i) a PDE1 Inhibitor, e.g., a compound according to any of Formulae I or 1.1-1.15, and (ii) a compound to promote wakefulness or regulate sleep, e.g., selected from (a) central nervous system stimulants, e.g., amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB), in free or pharmaceutically acceptable salt or form, to a human or animal patient in need thereof.

In another embodiment, the invention further provides methods of treatment or prophylaxis of a condition which may be alleviated by the enhancement of progesterone signaling comprising administering an effective amount of a Compound of the Invention, e.g., a compound according to any of Formulae I or 1.1-1.15, in free or pharmaceutically acceptable salt or form, to a human or animal patient in need thereof. Diseases or conditions that may be ameliorated by enhancement of progesterone signaling include, but are not limited to, female sexual dysfunction, secondary amenorrhea (e.g., exercise amenorrhea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmune disease, multiple sclerosis, prostate enlargement, prostate cancer, and hypothyroidism. For example, by enhancing progesterone signaling, the PDE1 inhibitors may be used to encourage egg implantation through effects on the lining of the uterus, and to help maintain pregnancy in women who are prone to miscarriage due to immune response to pregnancy or low progesterone function. The novel PDE1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously therapeutically effective amounts of
(i) a PDE1 Inhibitor, e.g., a compound according to any of Formulae I or 1.1-1.15, and
(ii) a hormone, e.g., selected from estrogen and estrogen analogues (e.g., estradiol, estriol, estradiol esters) and progesterone and progesterone analogues (e.g., progestins)
in free or pharmaceutically acceptable salt form, to a human or animal patient in need thereof.

The invention also provides a method for enhancing or potentiating dopamine D1 intracellular signaling activity in a cell or tissue comprising contacting said cell or tissue with an amount of a Compound of the Invention, e.g., a compound according to any of Formulae I or 1.1-1.15, in free or pharmaceutically acceptable salt form, sufficient to inhibit PDE1 activity.

The invention also provides a method for treating a PDE1-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., a compound according to any of Formulae I or 1.1-1.15, in free or pharmaceutically acceptable salt form, that inhibits PDE1, wherein PDE1 activity modulates phosphorylation of DARPP-32 and/or the GluR1 AMPA receptor.

In another aspect, the invention also provides a method for the treatment for glaucoma or elevated intraocular pressure comprising topical administration of a therapeutically effective amount of a PDE1 Inhibitor of the Invention, e.g., a compound according to any of Formulae I or 1.1-1.15, in free or pharmaceutically acceptable salt form, in an ophthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, e.g., a compound according to any of Formulae I or 1.1-1.15, in free or ophthalmically acceptable salt form, in combination or association with an ophthalmically acceptable diluent or carrier.

Optionally, the PDE1 inhibitor may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 Inhibitor of the Invention, e.g., a compound according to any of Formulae I, or 1.1-1.15, in free or pharmaceutically acceptable salt form, such that amount of the agent known to lower intraocular pressure and the amount of the PDE1 inhibitor in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with a PDE1 inhibitor may, for example, be selected from the existing drugs, e.g., a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g.,
1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics, such as epinephrine and dipivefrin (Propine), which increase outflow of aqueous humor through the trabecular meshwork and possibly through the uveoscleral outflow pathway, probably by a beta$_2$-agonist action.
5. Miotic agents (para-sympathomimetics), such as pilocarpine, which work by contraction of the ciliary muscle, tightening the trabecular meshwork and allowing increased outflow of the aqueous humour.
6. Carbonic anhydrase inhibitors, such as dorzolamide (Trusopt), brinzolamide (Azopt), and acetazolamide (Diamox), which lower secretion of aqueous humor by inhibiting carbonic anhydrase in the ciliary body.
7. Physostigmine is also used to treat glaucoma.

For example, the invention provides pharmaceutical compositions comprising a PDE1 Inhibitor of the Invention, e.g., a compound according to any of Formulae I or 1.1-1.15, in free or pharmaceutically acceptable salt form, and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine, in combination or association with a pharmaceutically acceptable diluent or carrier. For example, the invention provides ophthalmic formulations comprising a PDE-1 Inhibitor of the Invention, e.g., a compound according to any of Formulae I or 1.1-1.15, together with bimatoprost, abrimonidine, brimonidine, timolol, or combinations thereof, in free or ophthalmically acceptable salt form, in combination or association with an ophthalmically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $β_1$, or $β_2$, or $β_3$, depending on the appropriate therapeutic application. One can also select a muscarinic agonist selective for a particular receptor subtype such as $M_1$-$M_5$.

The PDE1 inhibitor may be administered in the form of an ophthalmic composition, which includes an ophthalmic solution, cream or ointment. The ophthalmic composition may additionally include an intraocular-pressure lowering agent.

In yet another example, the PDE1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, e.g., a compound according to any of Formulae I or 1.1-1.15, in free or pharmaceutically acceptable salt form, to a patient in need thereof.

PDE1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously therapeutically effective amounts of:
(i) a PDE1 Inhibitor of the invention, in free or pharmaceutically acceptable salt form; and
(ii) an antipsychotic, e.g.,
Typical antipsychotics, e.g.,
Butyrophenones, e.g. Haloperidol (Haldol, Serenace), Droperidol (Droleptan);
Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);
Thioxanthenes, e.g., Chlorprothixene, Flupenthixol (Depixol, Fluanxol), Thiothixene (Navane), Zuclopenthixol (Clopixol, Acuphase);
Atypical antipsychotics, e.g.,
Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine, 4-fluoro-2-((1-(2-(4-fluorophenyl)-2-oxoethyl)piperidin-4-yl)methyl) isoindolin-1-one, and 2-((1-(2-(4-fluorophenyl)-2-oxoethyl)piperidin-4-yl)methyl)isoindolin-1-one,
in free or pharmaceutically acceptable salt form, to a patient in need thereof.

In a particular embodiment, the Compounds of the Invention are particularly useful for the treatment or prophylaxis of schizophrenia.

Compounds of the Invention, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, in free or pharmaceutically acceptable salt form, to the eye of a patient in need thereof.

In yet another aspect, the invention provides a method for the treatment or prophylaxis of traumatic brain injury comprising administering a therapeutically effective amount of a PDE1 Inhibitor of the Invention, e.g., a compound according to any of Formulae I or 1.1-1.15, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury.

The present invention also provides
(i) a Compound of the Invention, e.g., a compound according to any of Formulae I or 1.1-1.15, as hereinbefore described, in free or pharmaceutically acceptable salt form for example for use in any method or in the treatment of any disease or condition as hereinbefore set forth,
(ii) the use of a Compound of the Invention, e.g., a compound according to any of Formulae I or 1.1-1.15, as hereinbefore described, in free or pharmaceutically acceptable salt form, (in the manufacture of a medicament) for treating any disease or condition as hereinbefore set forth, (iii) a pharmaceutical composition comprising a Compound of the Invention, e.g., a compound according to any of Formulae I or 1.1-1.15, as hereinbefore described, in free or pharmaceutically acceptable salt form, in combination or association with a pharmaceutically acceptable diluent or carrier, and (iv) a pharmaceutical composition comprising a Compound of the Invention, e.g., a compound according to any of Formulae I or 1.1-1.15, as hereinbefore described, in free or pharmaceutically acceptable salt form, in combination or association with a pharmaceutically acceptable diluent or carrier for use in the treatment of any disease or condition as hereinbefore set forth.

Therefore, the invention provides use of a Compound of the Invention, e.g., a compound according to any of Formulae I or 1.1-1.15, as hereinbefore described, in free or pharmaceutically acceptable salt form, or a Compound of the Invention in a pharmaceutical composition form (in the manufacture of a medicament) for the treatment or prophylactic treatment of any one or more of the following diseases: schizophrenia, Parkinson's disease, restless leg, tremors, dyskinesias, Huntington's disease, Alzheimer's disease, and/or drug-induced movement disorders; depression, attention deficit disorder, attention deficit hyperactivity disorder, bipolar illness, anxiety, sleep disorder, narcolepsy, cognitive impairment, e.g., cognitive impairment of schizophrenia, dementia, Tourette's syndrome, autism, fragile X syndrome, psychostimulant withdrawal, and/or drug addiction; cerebrovascular disease, stroke, congestive heart disease, angina, myocardial infarction, hypertension, pulmonary hypertension, e.g., pulmonary arterial hypertension, cardiovascular dysfunction due to muscular dystrophy (e.g., Duchenne muscular dystrophy), and/or sexual dysfunction; asthma, chronic obstructive pulmonary disease, and/or allergic rhinitis, as well as autoimmune and inflammatory diseases; and/or female sexual dysfunction, exercise amenorrhea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, and/or estrogen-induced endometrial hyperplasia and/or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling.

The invention also provides use of a Compound of the Invention, in free or pharmaceutically acceptable salt form, (the manufacture of a medicament) for the treatment or prophylactic treatment of any one or more of:

a) glaucoma, elevated intraocular pressure,
b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder,
c) traumatic brain injury, and/or
d) central and peripheral neurodegenerative disorders particularly those with inflammatory components.

The phrase "Compounds of the Invention" or "PDE1 Inhibitor of the Invention" encompasses any and all of the compounds disclosed herewith, e.g., compounds according to any of Formulae I or 1.1-1.15, as hereinbefore described, in free or salt form.

The words "treatment" and "treating" are to be understood accordingly as embracing prophylaxis and/or treatment or amelioration of symptoms of disease and/or treatment of the cause of the disease. In one embodiment, the invention provides a method for the treatment of the disease or disorder disclosed herein. In another embodiment, the invention provides a method for the prophylaxis of a disease or disorder as disclosed herein.

For methods of treatment, the word "effective amount" is intended to encompass a therapeutically effective amount to treat a specific disease or disorder.

The term "pulmonary hypertension" is intended to include pulmonary arterial hypertension and pulmonary venous hypertension.

The term "patient" includes human or non-human (i.e., animal) patients. In one embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention are in particular useful for the treatment of Parkinson's disease, narcolepsy, schizophrenia, cognitive impairment, and cognitive impairment of schizophrenia.

Compounds of the Invention, in free or pharmaceutically acceptable salt form, may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

Example 1. (6aR,9aS)-5-Methyl-3-(2,3,4,5,6-pentadeuterophenylamino)-2-(4-(6-fluoropyridin-2-yl)-benzyl)-5,6a,7,8,9,9a-hexahydrocyclopent[4,5]imidazo[1,2-a]pyrazolo[4,3-e]pyrimidin-4(2H)-one

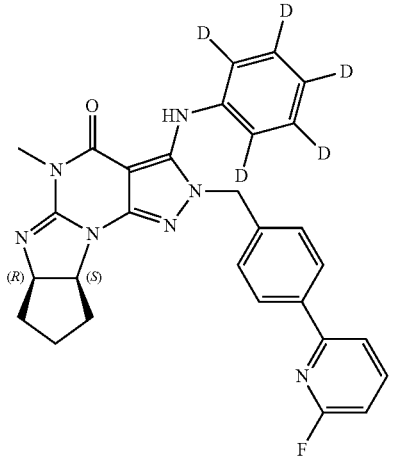

To a solution of (6aR,9aS)-5,6a,7,8,9,9a-hexahydro-3-chloro-5-methyl-2-(4-(6-fluoropyridin-2-yl)-benzyl)-cyclopent[4,5]imidazo[1,2-a]pyrazolo[4,3-e]pyrimidin-4(2H)-one (200 mg, 0.444 mmol) and 2,3,4,5,6-pentadeuteroaniline (162 μL, 1.8 mmol) in anhydrous 2-methyltetrahydrofuran (3 mL) is added LiHMDS (1.0 M in THF, 0.89 mL) dropwise at room temperature under argon atmosphere. The reaction mixture is gradually heated to 75° C. over a period of 90 min, and then heated at 75° C. for an hour. The mixture is cooled with an ice bath and then quenched by adding 0.2 mL of water. After solvent evaporation, the residue is dissolved in DMF and then filter with a 0.45 μm microfilter. The collected filtrated is purified with a semi-preparative HPLC system using a gradient of 0-70% acetonitrile in water containing 0.1% formic acid over 16 min to give (6aR,9aS)-5-methyl-3-(2,3,4,5,6-pentadeuterophenylamino)-2-(4-(6-fluoropyridin-2-yl)-benzyl)-5,6a,7,8,9,9a-hexahydrocyclopent[4,5]imidazo[1,2-a]pyrazolo[4,3-e]pyrimidin-4(2H)-one as a formate salt, which is dissolved in ethyl acetate, basified with 12.5 mL of 5% sodium carbonate, and then extracted with ethyl acetate three times. The combined organic phase is evaporated to dryness. The residue is dissolved in 4.5 mL of THF and then filter through a 0.45 μm microfilter. The filtrate is evaporated to dryness and further dried under vacuum to give (6aR,9aS)-5-methyl-3-(2,3,4,5,6-pentadeuterophenylamino)-2-(4-(6-fluoropyridin-2-yl)-benzyl)-5,6a,7,8,9,9a-hexahydrocyclopent[4,5]imidazo[1,2-a]pyrazolo[4,3-e]pyrimidin-4(2H)-one as a white solid (185.8 mg, 81.6% yield). $^1$H NMR (400 MHz, CDCl$_3$) δ7.88 (d, J=8.4 Hz, 2H), 7.88-7.77 (m, 1H), 7.58 (dd, J=7.5, 2.4 Hz, 1H), 7.05 (d, J=8.3 Hz, 2H), 6.90-6.80 (m, 2H), 4.94 (s, 2H), 4.82-4.68 (m, 2H), 3.34 (s, 3H), 2.27 (dd, J=12.4, 5.7 Hz, 1H), 2.09-1.91 (m, 1H), 1.91-1.67 (m, 3H), 1.67-1.49 (m, 1H). MS (ESI) m/z 513.3 [M+H]$^+$.

What is claimed is:

1. A compound of Formula I:

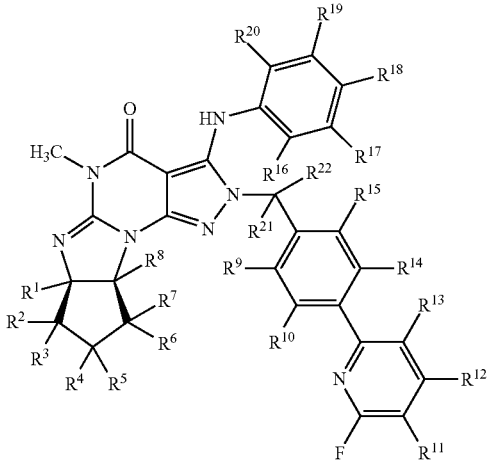

Formula I wherein $R_1$ through $R_8$, and $R_{16}$ through $R_{20}$ are each independently H or D (deuterium, $^2$H), and $R_9$ through $R_{15}$, $R_{21}$ and $R_{22}$ are each H, provided that at least one of $R_1$ through $R_8$ and $R_{16}$ through $R_{20}$ is D, in free or salt form.

2. The compound according to claim 1, wherein $R^1$ is D, and any one or more of $R^2$ through $R_8$ and $R_{16}$ through $R_{20}$ are D.

3. The compound according to claim 1, wherein $R^8$ is D, and any one or more of $R^1$ through $R^7$ and $R_{16}$ through $R_{20}$ are D.

4. The compound according to claim 1, wherein $R^4$ and $R^5$ are D, and any one or more of $R^1$ through $R^3$ and $R^6$ through $R_8$ and $R_{16}$ through $R_{20}$ are D.

5. The compound according to claim 1, wherein $R^{18}$ is D, and any one or more of $R^1$ through $R_8$ and $R_{16}$, $R_{17}$, $R_{19}$ and $R_{20}$ are D.

6. The compound according to claim 1, wherein $R^1$ is D.

7. The compound according to claim 1, wherein $R^8$ is D.

8. The compound according to claim 1, wherein $R^{18}$ is D.

9. The compound according to claim 1, wherein $R^1$ and $R^8$ are D.

10. The compound according to claim 1, wherein $R^1$ and $R^{18}$ are D.

11. The compound according to claim 1, wherein $R^1$, $R^8$ and $R^{18}$ are D.

12. The compound according to claim 1, wherein $R^{16}$ through $R^{20}$ are all D.

13. A pharmaceutical composition comprising a compound according to claim 1, in free or pharmaceutically acceptable salt form, in admixture with a pharmaceutically acceptable diluent or carrier.

14. A method of treating any of the following conditions: Parkinson's disease, cognitive impairment, cognitive impairment of schizophrenia, cerebrovascular disease, stroke, congestive heart disease, hypertension, pulmonary hypertension, and sexual dysfunction, comprising administering an effective amount of a pharmaceutical composition according to claim 13, to a patient in need thereof.

15. The method of claim 14, wherein the condition is Parkinson's disease.

16. The method of claim 14, wherein the condition is cognitive impairment.

17. The method of claim 14, wherein the condition is cognitive impairment of schizophrenia.

18. The method of claim 14, wherein the condition is female sexual dysfunction.

* * * * *

UNITED STATES PATENT AND TRADEMARK OFFICE
CERTIFICATE OF CORRECTION

PATENT NO. : 9,884,872 B2
APPLICATION NO. : 15/320280
DATED : February 6, 2018
INVENTOR(S) : Peng Li Page 1 of 2

It is certified that error appears in the above-identified patent and that said Letters Patent is hereby corrected as shown below:

In the Claims

Column 18, Lines 25-28 Claim 1:
"wherein $R_1$ through $R_8$, and $R_{16}$ through $R_{20}$ are each independently H or D (deuterium, $^2$H), and $R_9$ through $R_{15}$, $R_{21}$ and $R_{22}$ are each H, provided that at least one of $R_1$ through $R_8$ and $R_{16}$ through $R_{20}$ is D,"
Should be replaced with:
–wherein $R^1$ through $R^8$, and $R^{16}$ through $R^{20}$ are each independently H or D (deuterium, $^2$H), and $R^9$ through $R^{15}$, $R^{21}$ and $R^{22}$ are each H, provided that at least one of $R^1$ through $R^8$ and $R^{16}$ through $R^{20}$ is D,–

Column 18, Line 31 Claim 2:
"and any one or more of $R^2$ through $R_8$ and $R_{16}$ through $R_{20}$"
Should be replaced with:
–and any one or more of $R^2$ through $R^8$ and $R^{16}$ through $R^{20}$–

Column 18, Line 34 Claim 3:
"and any one or more of $R^1$ through $R^7$ and $R_{16}$ through $R_{20}$"
Should be replaced with:
–and any one or more of $R^1$ through $R^7$ and $R^{16}$ through $R^{20}$–

Column 18, Line 38 Claim 4:
"$R_8$ and $R_{16}$ through $R_{20}$ are D."
Should be replaced with:
–$R^8$ and $R^{16}$ through $R^{20}$ are D.–

Signed and Sealed this
Nineteenth Day of June, 2018

Andrei Iancu
*Director of the United States Patent and Trademark Office*

CERTIFICATE OF CORRECTION (continued)
U.S. Pat. No. 9,884,872 B2

Column 18, Lines 40-41 Claim 5:
"and any one or more of $R^1$ through $R_8$ and $R_{16}$, $R_{17}$, $R_{19}$ and $R_{20}$ are D."
Should be replaced with:
–and any one or more of $R^1$ through $R^8$ and $R^{16}$, $R^{17}$, $R^{19}$ and $R^{20}$ are D.–